US008263574B2

(12) United States Patent
Schaller et al.

(10) Patent No.: US 8,263,574 B2
(45) Date of Patent: Sep. 11, 2012

(54) TOPICAL FORMULATIONS FOR THE TREATMENT OF DEPRESSION WITH S ADENOSYL METHIONINE

(75) Inventors: James L. Schaller, Naples, FL (US); Ben Briggs, Coatesville, PA (US)

(73) Assignee: James L. Schaller, P.A., Naples, FL (US)

( * ) Notice: Subject to any disclaimer, the term of this patent is extended or adjusted under 35 U.S.C. 154(b) by 107 days.

(21) Appl. No.: 10/954,626

(22) Filed: Sep. 29, 2004

(65) Prior Publication Data

US 2006/0069059 A1    Mar. 30, 2006

(51) Int. Cl.
*A61K 31/7076* (2006.01)
*A61K 31/455* (2006.01)
*A61K 31/4415* (2006.01)

(52) U.S. Cl. ............. 514/46; 514/45; 514/350; 514/356

(58) Field of Classification Search .................... 514/45, 514/46, 350, 356
See application file for complete search history.

(56) References Cited

U.S. PATENT DOCUMENTS

| | | | | |
|---|---|---|---|---|
| 4,956,173 | A * | 9/1990 | Le Fur et al. | 424/63 |
| 5,073,546 | A * | 12/1991 | Zappia et al. | 514/46 |
| 5,455,234 | A | 10/1995 | Ahluwalia et al. | 514/46 |
| 5,496,827 | A * | 3/1996 | Patrick | 514/310 |
| 6,579,543 | B1 * | 6/2003 | McClung | 424/728 |
| 7,687,080 | B2 * | 3/2010 | Wolicki | 424/725 |

OTHER PUBLICATIONS

Murray, M.T. Encyclopedia of Nutritional Supplements, 1996, 100-105.*
Murray, Encyclopedia of Nutritional Supplements, 1996, pp. 100-105.*
Murray, Encyclopedia of Nutritional Supplements, 1996, pp. 365-368 and 373.*
Ghaouth, A,. E. et al, Phytopathology, 1997, 87, 772-79.*
eHow, 1999, pp. 1-4.*
Gupta, Shyam, *New Delivery Systems for Topical Nutraceutical (Nutracosmetic) and Cosmeceutical Formulations*, Business Briefing: Global Cosmetics Manufacturing 2004, pp. 1-5.
Whole Health Discount Center, http://www.health-pages.com/se/, c1997-2004, pp. 1-5.
Healthwell Homepage, SAMe, http://www.healthwell.com/healthnotes/healthnotes.cfm?ContentID=2907000, c2001, pp. 1-6.
http://consumerlab.com/results/same.asp, "Product Review: SAMe", © 2006, ConsumerLab.com, LLC, 6 pgs.
http://web.archive.org/web/*hh-/thewayup.com/, "The Way Up", © 1998-2004, Dr. Priscilla Slagle, 9 pgs.
Rosenbaum J.F. et al., "The antidepressant potential of oral S-adenosyl-l-methionine", *Acta Psychiatr Scand*, 1990, vol. 81, pp. 432-436.
Brown, Richard, M.D., et al., "S-Adenosylmethionine (SAMe) for Depression", *Psychiatric Annals*, vol. 32, 1, Jan. 2002; p. 29.
DeVanna, M. et al., "Oral S-Adenosyl-L-Methionine in Depression", *Current Therapeutic Research*, vol. 52, No. 3, Sep. 1992, pp. 478-485.
Schaller, J.L. et al., "SAMe use in Children and adolescents", *Eur. Child Adolescent Psychiatry*, Jan. 19, 2004, pp. 332-334.
"S-Adenosyl-L-Methlonine for Treatment of Depression, Osteoarthritis and Liver Disease", *Agency for Healthcare and Research and Quality; Evidence Report/Technology Assessment*, No. 64, pp. 1-3.
G.L. Cantoni; "The Nature of the Active Methyl Donor Formed Enzymatically From L-Methionine and Adenosinetriphosphate", vol. 74, May 9, 1952, pp. 2942-2943.
Brown, R. et al., "Stop Depression Now", SAMe Berkly, G.P. Putnam's & Sons, New York, 1999, pp. 1-7.
Agnoli A. et al., "Effect of S-Adenosyl-L-Methioninie (SAMe) Upon Depressive Symptoms", *J. Psych. Res.*, 1976, vol. 13, pp. 43-54, Pergamon Press.
Janicak PG, M.D., et al., "S-Adenosylmethionine in Depression—A Literature Review and Preliminary Report",*Ala. J. Med. Sci.*, vol. 25, 1988, pp. 306-313.
Knowlton, Leslie et al., "Investigating SAM-e", *Geriatric Times*, vol. II; Issue 5, © 2005, pp. 1-8.
Silveri, M.M. et al., "S-Adenosyl-L-Methionine: Effects on Brain Bioenergetic Status and Transverse Relaxation Time in Healthy Subjects", *Soc. Bio. Psych.*, © 2003, pp. 833-839.
Bottiglieri, T., "S-Adenosyl-L-Methionine (SAMe): from the bench to the bedside-molecular basis of a pielotrophic molecule", *Am J Clin Nutr*, 2002; 76 (suppl): 1151S-1157S.
Benelli, A et al., "Influence of S-adenosyl-L-methionine on chronic mild stress-induced anhedonia in castrated rats", *British Journal of Pharmacology*, 1999, vol. 127, pp. 645-654.
Chiaie, Roberto Delle et al., "Efficacy and tolerability of oral and intramuscular S-adenosyl-L-methionine 1,4-butanedisulfonate (SAMe) in the treatment of major depression: comparison with imipramine in 2 multicenter studies", *Am J Clin Nutr*; 2002, vol. 76 (suppl): 1172S-6S, 2002.
Pancheri, P. et al., "A double-blind, randomized parallel-group, efficacy and safety study of intramuscular S-adenosyl-L-Meethionine 1,4-butanedisulphonate (SAMe) versus imipramine in patients with major depressive disorder", *Int. J. of Neuropsychopharmacology*, 2002, vol. 5, pp. 287-294.
Saletu, B. et al., "Electrophysiological neuroimaging of the central effects of S-adenosyl-L-methionine by mapping of electroencephalograms and event-related potentials and low-resolution brain electromagnetic tomography", *Am J Clin Nutr*, 2002; 76 (suppl):1162S-71S.
Fava, M. et al., "Rapidity of onset of the antidepressant effect of parenteral S-adenosyl-L-Methionine", *Psych Research*, 56, 1995, pp. 295-297.
Kovacs, M., Ph.D., "The Children's Depression, Inventory", *Psychopharmacology Bulletin*, vol. 21, No. 4, 1985, pp. 995-998.
Warrington, S.J. et al., "The Cardiovascular effects of Antidepressants", *Psychological Medicine; Monograph Supplement 16*, Cambridge University Press, 1989, pp. 1-40.

(Continued)

*Primary Examiner* — Shaojia Anna Jiang
*Assistant Examiner* — Ganapathy Krishnan
(74) *Attorney, Agent, or Firm* — Dorsey & Whitney LLP

(57) ABSTRACT

Disclosed herein are topical formulations for treating depression with S adenosyl methionine (SAM-e) The topical formulations contain at least 35% wt/wt of SAM-e partially dissolved in aqueous and lipophilic phases of an emulsion and the emulsion is stable from separation of phases for a period of at least 30 days despite the high concentration of SAM-e. Also provided are methods for making such compositions and methods of treating depression using the same.

50 Claims, No Drawings

OTHER PUBLICATIONS

Davidson, Jonathan, M.D. et al., "The Underrecognition and Undertreatment of Depression: What is the Breadth and Depth of the Problem?", J. Clin. Psychiatry, 1999, vol. 60 ( Supp. 7 ), pp. 4-11.

Elkins, Rita., M.H., "SAMe—The Remarkable Substance that Promotes Detoxification, Relieves Arthritis and Fights Depression", Woodland Publishing, Pleasant Grove, UT, 5 pgs.

* cited by examiner

TOPICAL FORMULATIONS FOR THE TREATMENT OF DEPRESSION WITH S ADENOSYL METHIONINE

TECHNICAL FIELD

This invention relates to topical formulations for the treatment of depression with S-adenosyl methionine.

BACKGROUND OF THE INVENTION

S-adenosyl methionine (SAM-e) is made by the body and is a metabolite present in all living cells. Unlike current psychopharmacologic options for treating depression, SAM-e is an agent that is indigenous to the body, and may offer an alternative option for treatment-resistant Major Depression in children and adolescents. The chemical structure of SAM-e was described as early as 1952 (Cantoni G L. *The nature of the active methyl donor formed enzymatically from L-methionine and adenosinetriphosphate. J Am Chem Soc* 1952; 74:2942-2943.). It has been in use for decades in Europe, and is a prescription medication in such countries as Italy, Spain, Germany and Russia. (Brown R, Bottiglieri T, Colman C. *Stop Depression Now: SAMe* 1999:Berkley, N.Y., pg. 5).

The first clinical study of SAM-e's use for depression appears to have been conducted in the 1970s (Agnoli A, Andreoli V, Casacchia M, Cerbo R (1976), *Effect of S-adenosyl-L-methionine (SAMe) upon depressive symptoms. J Psychiatr Res* 1976; 13:43-54) and since then has been repeatedly studied. Specifically, SAM-e has been found effective for treating major depressive disorder in 13 trials comparing it to placebo, and 19 trials comparing it to tricyclic antidepressants with more than 1,400 patients studied. From 1973 to 1988, 14 double-blind, European studies showed that intravenous and intramuscular preparations of SAM-e were more effective than placebo and comparable to imipramine, amitriptyline and clomipramine for treatment of major depression. Since then, SAM-e has been evaluated for various disorders in more than 75 clinical trials involving over 23,000 people (Janicak P G, Lipinski J, Davis J M et al. (1988), *S-adenosylmethionine in depression. A literature review and preliminary report. Ala J Med Sci* 1988; 25:306-313; Knowlton L. *Investigating SAM-e. Geriatric Times* 2001, www.geriatrictimes.com/g010923.html.).

The mechanism for SAM-e's effectiveness in Major Depression is unclear (Silveri M M, Parow A M, Villafuerte R A, Damico K E, Goren J, Stoll A L, Cohen B M, Renshaw P F. *S-adenosyl-L-methionine: effects on brain bioenergetic status and transverse relaxation time in healthy subjects Biol Psychiatry* 2003; 54:833-9) Yet some propose a mechanism that since SAM-e functions as a precursor to methylation, aminopropylation and transulfuration pathways, it is the most important methyl donor in the brain and is essential for polyamine synthesis. Brain methyl group deficiency has been implicated in depression, and polyamine phosphorylation enhancement of neuronal proteins may be involved in its antidepressant mechanisms (Bottiglieri T. *S-Adenosyl-L-methionine (SAMe): from the bench to the bedside—molecular basis of a pleiotrophic molecule. Am J Clin Nutr* 2002; 76:1151S-7S.; Benelli A, Filaferro M, Bertolini A, Genedani S. *Influence of S-adenosyl-L-methionine on chronic mild stress-induced anhedonia in castrated rats. Br J Pharmacol* 1999; 127:645-54).

SAM-e has been studied in adults using both IM and oral routes. For example, two multicenter double-blind studies, examined both intramuscular (400 mg) and oral SAM-e (1600 mg) in adults and compared it with 150 mg of imipramine (IMI) in patients with Major Depression. Specifically, one study noted antidepressant effects in a double blind multi-center study in which 147 treated patients were given SAM-e intramuscularly at a dose of 400 mg/d vs. 148 patients treated with 150 mg/d of oral imipramine (IMI) over 4 weeks. A Major Depression diagnosis included a baseline score on the 21-item Hamilton Depression Rating Scale (HAMD) of $>/=18$. A "response" included a fall in HAMD scores of at least 50% with respect to baseline. SAM-e and IMI did not differ significantly on any efficacy measure. SAM-e and IMI both showed a significant antidepressant response—a HAMD improvement of at least 50%. These data show 400 mg/d of intramuscular SAM-e to be comparable to 150 mg/d of oral IMI in terms of anti-depressive efficacy. In the other study, a total of 143 patients received 1600 mg of oral SAM-e and 138 received IMI for a period of 6 weeks. Therefore, both intramuscular (400 mg) and oral SAM-e (1600 mg) in adults was comparable to 150 mg of imipramine (IMI). SAM-e was better tolerated than IMI in both studies (Delle Chiaie R, Pancheri P, Sapicchio P. *Efficacy and tolerability of oral and intramuscular S-adenosyl-L-methionine 1,4-butanedisulfonate (SAMe) in the treatment of major depression: comparison with imipramine in 2 multicenter studies. Am J Clin Nutr* 2002; 76:1172S-6S; Pancheri P, Scapicchio P, Chiaie R D. *A double-blind, randomized parallel-group, efficacy and safety study of intramuscular S-adenosyl-L-methionine 1,4-butanedisulphonate (SAMe) versus imipramine in patients with major depressive disorder. Int J Neuropsychopharmacol.* 2002; 5:287-94).

Neurology studies support SAM-e's antidepressant effects. In a double-blind, placebo-controlled, crossover study, using random infusions of 800 mg of SAM-e Electroencephalograms (EEGs), event-related potentials (ERPs) and low-resolution brain electromagnetic tomography identified SAM-e as an antidepressant with effects greater than placebo (Saletu B, Anderer P, Di Padova C, Assandri A, Saletu-Zyhlarz G M. *Electrophysiological neuroimaging of the central effects of S-adenosyl-L-methionine by mapping of electroencephalograms and event-related potentials and low-resolution brain electromagnetic tomography. Am J Clin Nutr* 2002; 76:1162S-71S).

Further, SAM-e appears to have a fairly rapid onset of action. When 195 patients were given 400 mg of intramuscular SAM-e for 15 days, their depressive symptoms showed remission on both day 7 and 15 of treatment with SAM-e (Fava M, Giannelli A, Rapisarda V, Patralia A, Guaraldi G P. *Rapidity of onset of the antidepressant effect of parenteral S-adenosyl-L-methionine. Psychiatry Res* 1995; 56:295-7).

Child Case Studies

Two girls aged 11 and 8 were brought in for a consult by a pediatrician and his spouse, a nutritionist. Both parents had studied SAM-e, and preferred "a trial" before traditional antidepressants. They noted SAM-e was in "most large pharmacies" and believed "it should be considered more in depression treatment." Both parents had a strong family history of Dysthymia or Major Depression (MD). Both parents were taking SAM-e themselves and "felt" it provided full remission of their depression, at 1200-1400 mg per day.

Case 1. An 11-year-old girl (34 kg.) developed increased irritability, boredom, eccentric crying, withdrawal, decreased appetite, middle insomnia, new school performance problems and sadness. She began to discuss death themes and became preoccupied with heaven, despite no new exposures to these topics. She met DSM-IV TR criteria for Major Depression, had no significant stressors in her life, and on the Children's Depression Inventory (CDI) scored a 34.

She was placed on a 200 mg SAM-e enteric-coated tablet each morning, before eating for a week. Subsequently, the dose was raised to 400 mg. She showed modest improvement over 3 weeks on this higher dose. Improvement began after 4 days on 400 mg. At three weeks, it was increased to 600 mg a day, with rapid and complete resolution of her depressive symptoms in 2 days. She had no signs of mania, anxiety, insomnia, diarrhea, abdominal pain or nausea. Her CDI fell to a 4. She has been on this dose for over 6 months.

Case 2. An 8 year-old girl (24 kg.) developed new problems with crying, sadness, decreased play, and an inability to be consoled. She made new negative identity comments, i.e., "I'm no good Mommy." The child was well liked by adults and peers, but felt "no one liked her," She also began saying she "hated school" even though she was in the top ⅓rd of her class. Her symptoms began 4-5 months after her sister's MD began. She met DSM-IV TR criteria for Major Depression and on the Children's Depression Inventory scored 29.

She was treated with 200 mg of SAM-e and in 2 days showed signs of improvement, especially in increased play and decreased crying. In 11 days, the child was at baseline with no side effects. Her CDI decreased to 6 and 7. After 3 months, she was "a little sad like before" per her mother, and was increased to 200 mg each am and afternoon with a CDI of 6. She has remained on this dose for over 6 months.

Case 3. A 16 year-old male (86 kg.), unrelated to the girls described above, was diagnosed with Major Depression and Oppositional Defiant Disorder based on DSM-IV TR criteria from a clinical interview with parents and patient. He refused diagnostic scales. His parents reported a 1½ year history of irritability, boredom, reactivity, decreased interest in all activities but computer games, sadness, excess sleep, fatigue, hopelessness, and trouble concentrating. His school materials showed a similar time line and his grades had fallen from the B/C level to D's and F's. Extensive laboratory testing and family doctor physical exam were negative.

The youth refused a trial of traditional antidepressants, saying, he did not want "a drug" or "something which was foreign or poison." After extensive discussion with the patient and his parents, he was willing to try SAM-e, because it was "natural" and "made in the body." Both parents and patient understood that we were not aware of "studies in adolescents."

The patient was started on 200 mg and surprisingly raised himself to 1800 mg in a 10-day period. He developed a slight tremor and slight anxiety. When both dose and side effects were noticed, and that he had ignored the suggested taper, his dose was reduced to 1400 mg with loss of both side effects. His mood and function improved to his baseline over 1-2 weeks according to parents, teacher and psychiatrist. Yet he had residual oppositionality. After 2-3 months the youth stopped his SAM-e due to "being sick of all the pills." He had been taking 7×200 mg tablets daily. He relapsed over the course of 3 weeks to "½" his initial baseline depression per patient and parents. Again, he refused quantitative depression scales. Behaviorally, he stopped returning calls, became bored again, and had decreased homework performance with no identifiable new stressors. Restoring the SAM-e to three 400 mg tablets—800 mg per am and 400 after school—restored him to baseline in 5-8 days from parent report confirmed with diagnostic interview. He has remained on this dosing for approximately 22 weeks.

Because the clinical world has very finite treatment options for treatment of resistant depression in youth, SAM-e should be seriously considered as an option, as a primary agent or as an add-on to antidepressants, omega 3 essential fatty acids or mood stabilizers. However, because of the resistance of some children and parents to taking "drugs" in oral or injection form and because of the stigma that may be attached thereto, there is a need in the art to deliver therapeutically effective amounts of SAM-e in ways other than by injection or oral administration. In addition, oral SAM-e has gastrointestinal side effects such as diarrhea, cramping and nausea, which can occur at sub-therapeutic doses.

SUMMARY OF THE INVENTION

Provided herein are topical composition for treating depression with S-adenosyl methionine. The compositions include, a base emulsion that includes a lipophilic component and an aqueous component, S-adenosyl methionine at least partially dissolved in the base and present in an amount of at least 35% wt/wt of the composition, a pH adjusting component to bring the pH of the composition between 6.5 and 7.5, and the composition is formulated to be stable against separation of the emulsion for a period of at least 30 days when stored at room temperature. In particular embodiments, the base emulsion includes 55%-85% of the aqueous component and 45%-15% of the lipophilic component. In other particular embodiments, the base emulsion includes 65%-75% of the aqueous component and 35%-25% of the lipophilic component.

In certain embodiments, the SAM-e is partly dissolved in the aqueous phase, partly dissolved in the lipophilic phase, and partially remains in a solid phase in suspension in the base. In other embodiments, the SAM-e is partly dissolved in the aqueous phase, partly dissolved in the lipophilic phase, and the part that is dissolved in the aqueous phase includes a part dissolved into an interior aqueous compartment or lamella of a micelle where the aqueous compartment is encapsulated or interspersed with the lipophilic component.

DETAILED DESCRIPTION OF PREFERRED EMBODIMENTS

Prior to setting forth the invention in detail, certain terms are defined herein to aid in a better understanding of the invention. These terms are intended to have the same meaning as conventionally understood by one of ordinary skill in the art, except where various nuances of such conventional understandings may conflict with the meanings set forth herein, in which case the meanings set forth herein control.

An "oil" is a composition containing at least 95% wt of a lipophilic substance. Example lipophilic substances include but are not limited to naturally occurring and synthetic oils, fats, fatty acids, lecithins, triglycerides and the like as well as combinations of the same.

An "emulsion" is a composition containing a mixture of non-miscible components homogenously blended together. In particular embodiments, the non-miscilble components include a lipophilic component and an aqueous component.

A "lotion" is an emulsion having a viscosity of between 100 and 1000 centistokes.

A "cream" is an emulsion having a viscosity of greater than 1000 centistokes, typically in the range of 20,000-50,000 centistokes.

A "paste" is a liquid or emulsion having solid material homogenously suspended therein, typically in a lotion cream or gel.

A "gel" is a composition containing a thickening agent or polymeric material dissolved or suspended in a liquid. The liquid may include a lipophilic component, an aqueous component or both. Some emulsions may be gels or otherwise include a gel component. Some gels, however, are not emulsions because some do not contain a homogenized blend of immiscible components.

There is provided herein, stable transdermal formulations systems to topically deliver S-adenosylmethionine (also known as adenomethionine or AdeMet and abbreviated herein as SAM-e) directly to the bloodstream in amounts therapeutically effective for the treatment of depression. The transdermal formulation systems provided herein allow SAM-e to penetrate the stratum corneium to deliver the SAM-e to the capillary vasculature, thereby achieving measurable systemic blood levels. The formulations are designed for transdermal administration because oral preparations of SAM-e have considerable gastrointestinal side effects at dosages required to treat depression. The delivery systems provided herein eliminate gastrointestinal side effects and the first pass effect associated with oral administration of SAM-e. It also allows for greater flexibility, especially in regards to controlling pediatric dosages and by removing the stigma and compliance issues attached to the use of tablets.

Use of SAM-e for transdermal delivery in an amount effective to treat depression presents several obstacles overcome by the compositions provided herein. First, the amount of SAM-e necessary to treat depression is relatively high, i.e., at least about 350 mg per dose. While topical formulations for delivering such a high dosages could be prepared by dissolving the SAM-e in relatively large amount of solvent, the amount of the solvent required to solubilize a therapeutically effective amount of SAM-e would be so large as to require applying the composition to a relatively large area of the skin. Solubilized SAM-e is an odious composition, therefore, distribution of SAM-e over a large area of skin is undesirable to the user, making compliance with a therapeutic scheduled less likely.

It is therefore desirable that the SAM-e be delivered in therapeutic amounts in a relatively small volume for topical administration, typically in a volume of less than 5 ml, less than 3 ml and most desirably in about 1 ml or less. In embodiments where the SAM-e is delivered in a volume of about 1 ml or less, the topical delivery system can be spread over a relatively small area of the skin easily covered by an adhesive band to mask the odor. To deliver SAM-e in a therapeutic amount necessary to treat depression in a volume of 1 ml or less requires a delivery formulation containing at least 35% wt/wt of SAM-e. Unfortunately, it has been discovered that preparing SAM-e formulations for topical delivery at such concentrations typically results in a composition that is unstable, i.e., one that separates into phases, oxidizes or otherwise breaks down in hours or maximally, within about 14 days, when stored at room temperature or in a refrigerator.

To solve this problem, there are provided compositions that are stable from separation into phases for a period of at least 30 days when stored at room temperature. In one aspect, the SAM-e in the compositions provided herein is apportioned between, and at least partially solubilized in, at least two separate components of a base emulsion. The base emulsion may be a lotion, a cream, a gel or a paste. A first portion of the SAM-e is solubilized in an aqueous component of the emulsion and the second portion is solubilized in a lipophilic portion of the emulsion.

In another aspect, the SAM-e in the compositions provided herein is not only apportioned and at least partially solubilized in both the aqueous and lipophilic portions of the base emulsion, but is also encapsulated in micelles that are formed in the base. The micelles have a lipophilic membrane surrounding an aqueous interior compartment made of a second portion of the aqueous component. The structure of the micelles formed may include multilamellar or unilamellar vesicles or unstructured micellular aggregates and/or combinations of the same. A portion of the SAM-e is dissolved in the aqueous compartments of the micelle.

In yet another aspect, the SAM-e in the compositions provided herein is apportioned into three or four parts. The first portion is solubilized in the aqueous component of the base, the second portion is solubilized in the lipophilic component, and a third portion of the SAM-e remains suspended in a solid phase in the base emulsion as fine particulate. In this case, the SAM-e compositions are in the form of a paste. The suspension of a solid phase portion of the SAM-e in the paste can be used whether or not there is also a forth portion of the SAM-e encapsulated in micelles.

The size of the solid phase SAM-e particulate matter suspended in the base emulsion may be important to effectiveness of the composition. While not being bound by theory, it is believed that as the solubilized form of SAM-e is absorbed from the base through the skin into the blood vessels, the remaining portion of the solid SAM-e in suspension gradually dissolves into the base by bulk flow to replace the SAM-e transferred to the blood system. Hence, the subject receives a gradual dosing of the SAM-e with each application. Advantageously, this allows the SAM-e to be more effective at lower dosages than required for oral or intravenous administration. If the SAM-e particles are too large, they will not efficiently dissolve into the base over time and transfer into the blood vessels in a time that would be therapeutically effective. Accordingly, the size of the SAM-e particles in the suspended phase of the composition should be less than 500 microns, or less than 100 microns or in some embodiments, less than 10 microns in size.

To make the various embodiments of the topical formulation systems provided herein, the total amount of dry SAM-e powder to be used in the composition is first ground into a very fine powder before being thoroughly mixed into the base emulsion (the first base). In a typical procedure, 40 g of SAM-e powder (free base) is thoroughly mixed with 40 g of the first base. The mixing into the base results in solubilization of a portion of the SAM-e into both the aqueous and lipophilic components of the emulsion. The composition initially appears as a paste with a noticeable gritty texture. The paste is further homogenized by milling in a lotion press, which causes further solubilization of some of the SAM-e, further reduces the size of the suspended particles to less than about 500 microns, or less than about 100 microns, and results in the formation of micelle vesicles and/or aggregates with an apportionment of a portion of the SAM-e into the interior aqueous compartments of the micelles. The paste is milled until it no longer has a noticeable gritty texture, although it still may contain a certain portion of solid SAM-e suspended in the emulsion. Finally a sufficient amount of a second base, which may be the same as the first base or may be another base that does not cause separation, is thoroughly mixed into the milled product to form a final product with a weight of 100 g.

The inventors have discovered that to make a composition that does not separate, it is critical that the SAM-e be dissolved in a first base that contains 55%-85% of an aqueous component and 45%-15% of a lipophilic component. The compositions are particularly suitable for formulations with the free base forms of SAM-e. In certain cases, specialty salts of SAM-e, such as taurine salts, specifically formulated to increase the lipophilic character of SAM-e may be useful in certain embodiments with different ranges of aqueous and lipophilic components. In other cases, taurine salts of SAM-e are specifically not used in the compositions provided herein.

In particular embodiments, the base emulsion includes 65%-75% of the aqueous component and 35%-25% of the lipophilic component. In addition, the final composition should have the same relative distribution of aqueous and lipophilic components.

One example of a commercially available base emulsion suitable for use in the delivery systems provided herein includes, but is not limited to, LIPODERM™ lipophilic liposomic cream (a mixture of about 60-80% wt/wt water, with glycerin, C12-15 alkyl benzoate, glyceryl stearate, dimethicone, cetearyl alcohol, cetearyl glucoside, polyacrylamide, cetyl alcohol, magnesium aluminum silicate, xanthan gum, *aloe vera* (*aloe barbadensis*), tocopheryl acetate (vitamin E acetate), *prunus amygadalus amara* (bitter almond) kernel oil, *vitis vinifera* (Grape) seed extract, *triticum vulgare* (wheat) germ oil, retinyl palmitate (vitamin A palmitate), ascorbyl palmitate (vitamin C palmitate), Pro-Lipo Multiemulsion Liposomic System, tetrasodium EDTA, phenoxyethanol, sodium hydroxymethylglycinate). PCCA, Houston, Tex.

The composition in LIPODERM™ lipophilic liposomic cream is particularly suitable when formulated in accordance with the guidance provided herein. For example, the inventors have discovered that surprisingly, to formulate a composition that does not separate, it is important that the SAM-e be dissolved in a suitable mixed phase emulsion such as LIPODERM™ lipophilic liposomic cream first, and not be dissolved in an aqueous, alcoholic, glycol, ethoxy, or oil based solvent prior to being milled into the base. If, for example, the SAM-e is dissolved into water or oil first, the subsequent addition of LIPODERM™ lipophilic liposomic cream or PCCA COSMETIC HRT® base (a mixture of water, caprylic and capric triglycerides, polyacrylamide C13-14, isoparaffin/laureth-7, SD alcohol, phenoxyethanol, *aloe vera* gel, vitamin E acetate) results in a composition that still separates in 3 to 14 days at room temperature (see failed batches 11-16 mentioned below). Moreover, the inventors have discovered that pH, temperature and humidity are important factors to control during the formulation to make a composition that is stable. SAM-e is a highly unstable, hygroscopic molecule that needs to be stored, handled, and therefore, the compositions should be prepared in a humidity-controlled environment of optimally less than 40% humidity, at temperatures optimally ranging between 65-75° F., and a pH of 6.5-7.5.

To further solubilize the SAM-e and form a final lotion, cream or paste for topical administration, a suitable diluent is thoroughly mixed into the milled paste to obtain a final composition having at least 35% wt/wt SAM-e. A suitable diluent is one that will form a stable, non-separable composition when mixed into the milled paste. As a general guide, the diluent should be selected so that the final composition retains 55%-85%, or in particular embodiments, 65%-75% of the aqueous component and 45%-15%, or in particular embodiments, 35%-25% of the lipophilic component. Moreover, the final aqueous phase of the composition should contain less than 5% of an alcohol having 3 carbons or less, and less than 5% of a glycol or ethoxy compound of 3 carbons or less. Ethanol and isopropanol should particularly be limited because diluents or bases containing greater that 5% of any one of these solvents have a tendency to cause separation of the final composition. However, higher amounts of the solvents to be avoided may be used in instances where the diluent is a gel. In one embodiment, the diluent is a second portion of the same base emulsion that was used to form the paste. In other embodiments the diluent may be a second base emulsion different from the first. In other embodiments, the diluent may include a gel that is added to the paste alone, or in addition to a second portion of the base. Suitable commercially available second diluents that are base emulsions, thickening agents or gels include, but are not limited to, LIPODERM™ lipophilic liposomic cream, DEMI-GEL™ emulsion (which is a mixture of 4% lecithin isopropyl palmitate containing lecithin soya granular, isopropyl palmitate NF, sorbic acid NF) and 96% Pluronic Gel 20% (propylparaben NF, methylparaben NF, imidazolidinyl urea NF, PLURONIC®F127NF block copolymer surfactant, purified water) or KRISGEL™ 100 thickening agent as formulated by the manufacturer as of the date of filing of the present application. Each are available from PCCA, Houston Tex. PLURONIC® F127 NF block copolymer surfactant is available from BASF, Mount Olive, NJ. Other diluents, thickening agents or gels that may be added in limited amounts so as not to cause separation of the final solution (i.e., added to less than 10% of the wt of the final composition) may include:

PLO-GEL™ (20% lecithin isopropyl palmitate solution (lecithin soya granular, isopropyl palmitate NF, sorbic acid NF)) and (80% of Pluronic Gel 20% (propylparaben NF, methylparaben NF, imidazolidinyl urea NF, PLURONIC®F127 NF block copolymer surfactant, purified water)). PCCA, Houston Tex.

*Aloe vera* gel, (*alove vera* gel, tiethanolamine, tocopheryl acetate, carbomer 940, tetrasodium EDTA, DMDM hydantoin, diazolidinyl urea. Fruit Of The Earth, Irving Tex.

Pluronic Gel (a mixture of propylparaben NF, methylparaben NF, Imidazolidinyl Urea NF, PLURONIC®F127 block copolymer surfactant), PCCA, Houston, Tex.

Although use of commercially available base emulsions, gels and diluents may be practiced in certain embodiments, the compositions provided herein may be formulated with any suitable emulsion that includes a at percenage of the aqueous component of 55%-85%, or in particular embodiments, 65%-75% and a lipophilic component of 45%-15%, or in particular embodiments, 35%-25% wt/wt.

The aqueous component includes water, and may include one or more hydrophilic solutes or solvents. As used herein, a hydrophilic solute is a substance that more readily dissolves in water than in a lipid. A hydrophilic solvent is one that is more miscible with water than with a lipid, and that more readily dissolves a hydrophilic solute than a lipid. In various embodiments, the aqueous component may include, as a fractional weight of the aqueous component, 5% or less of glycerin (glycerol); 5% or less of a small chain alcohol of three carbons or less; 5% or less of small chain polyol; glycol or ethoxy glycol of 3 carbons or less; 5% or less of a sugar or amino sugar of 6 carbons or less; 5% or less of an organic acid or poly acid of 4 carbons or less; 5% or less of a hydrophilic polymer; and combinations of the same. In certain particular embodiments, the aqueous component includes water and from 0.5 to 5% glycerin as a fractional weight of the aqueous component. In certain other embodiments the aqueous component may further include 0 to 3% EDTA as a fractional weight of the aqueous component.

The lipophilic component of the base includes, in various alternative embodiments, at least 3, at least 4, at least 5, or at least 6 lipophilic substances selected from the group consisting of lecithin, C12-C15 alkyl benzoate, palmitate, isopropyl palmitate, vitamin A palmitate, vitamin C palmitate, butylated hydroxytoluene, cetyl alcohol, stearyl alcohol, stearic acid, glyceryl monostearate, isopropyl myristate, simethicone, polyoxyl stearate, glyceryl stearate, cetearyl alcohol, cetearyl glucoside, cetyl alcohol, bitter almond kernel oil, grape seed extract and wheat germ oil. Other lipophilic substances that may be added to the lipophilic component include, but are not limited to dimethicone, carbomer 940, glyceryl monostearate, sodium laurel sulfate, paraffin, mineral oil, petrolatum, avocado oil, olive oil, peanut oil, castor oil, sesame oil, canola oil, grape seed oil, linseed oil, borage oil, sodium laureth sulfate, ceteareth-20, polyethylene glycol monostearate, iospropyl palmitate, cetyl myristoleate, cetyl esters wax, oleic acid or KRIS-ESTER™ 236 (as formulated by PCCA as of the filing date of this application.).

Accordingly, there are a large number of possible formulations of the base used in the topical delivery system provided herein. What is required is that the composition contain the foregoing wt/wt % distribution of aqueous and lipophilic components homogenously mixed with at least 35% wt/wt of SAM-e and that the composition remains stable from separation for at least 30 days at room temperature or when refrigerated.

The inventors have discovered that to form a composition of at least 35% wt/wt SAM-e suitable for topical administration and that is stable from separation for at least 30 days, requires that at least one, and preferably all, of the following be accomplished: (1) the base into which the SAM-e is first dissolved should include both a lipophilic component and an aqueous component; (2) a thickening agent or gel should be included in the composition either as a component of the base or added to the base SAM-e mixture; (3) the pH of the composition should be adjusted, and preferably buffered, to between 6.5 and 7.5; (4) the SAM-e should be mechanically worked into the base using a lotion mill or other suitable machine for ensuring homogenous blending of the base/SAM-e mixture prior to addition of other components of the composition; (5) the composition should include an anti-oxidant agent and an antibacterial and/or antifungal agent as a further preservative; (6) the composition should include a vasodilation agent to promote penetration of the SAM-e into the blood vessels.

By way of example, suitable anti-oxidant agents include, but are not limited to: vitamin A, vitamin E, deoxy-D-glucose, dithiothreitol, citric acid, grape seed extract, alpha lipoic acid, glutathione (reduced), N-acetyl cysteine, olive leaf extract, ascorbyl palmitate, benzoic acid, benzethonium chloride, benzyl alcohol, butylated hydroxyanisole, butylated hydroxytoluene, chlorobutanol, dehydroacetic acid, ethylenediamine, ethylparaben, ethyl vanillin, hypophosphorous acid, malic acid, maleic acid, monothioglycerol, phenol, phenylethyl alcohol, phenylmercuric nitrate, potassium benzoate, sodium benzoate, potassium metabisulfite, potassium sorbate, propyl gallate BP, sassafras oil, sodium bisulfite, sodium metabisulfite, sodium propionate, sorbic acid, sulfur dioxide and thimerosal.

Suitable anti-bacterial and/or antifungal agents include but are not limited to, deoxy-D-glucose, methylparaben, propylparaben, benzalkonium chloride, β-1,3-D-glucan, oregano oil., and any of various known topical antibiotics.

Suitable vasodilation agents include, but are not limited to, pyridoxyl-5-phosphate, niacinamide, DMSO, pentoxifylline, ibuprofen, horse chestnut extract (*Aesculus hippocastanum*) and pyridoxine. Folic acid, although potentially useful, should be avoided, as this tends to form an inelegant composition in terms of color.

In addition, the compositions may optionally include one or more compatible various fragrant oils or other compatible fragrant substances. Compatible oils and fragrances include, by way of example, cinnamon leaf oil, vanilla extract, lime oil, orange oil, lavender oil, pine oil, clove oil, lemon oil, tangerine oil, rose oil, rose geranium oil, patchouli oil, teaberry oil, oil of wintergreen, spearmint oil, peppermint oil, oil of sage, anise oil, caraway oil, cardamon oil, glycyrrhiza extract, nutmeg oil, and ethyl vanillin.

To use the compositions provided herein for treatment of depression, the compositions are typically provided in a pump, syringe, tube or other suitable container, and preferably a container that minimizes exposure of the contents to air. A therapeutic amount of about 1-2 ml of the composition is rubbed into a site of about 1-3 square centimeters on the patient's skin, preferably at a place that will be covered by clothing. In an alternate or additional practice, the composition may be covered by an adhesive bandage to further mask the odor of the SAM-e. Typically, a therapeutic dose for treatment of depression with SAM-e is approximately 800 to 1600 mg/day for the average adult subject. Accordingly, in using an example composition provided herein at a concentration of 40% wt/wt, the subject would be administered the composition at periodic intervals 2 to 4 times a day.

As a further guide to making the compositions of the present invention, it is helpful to illustrate what formulations do not work to teach the skilled person what to avoid. Accordingly, the following batches each illustrate formulations that result in compositions that failed due to instability of phases of the emulsion, poor consistency, lack of cosmetic elegance, oxidation, the inability to maintain therapeutic amounts of SAM-e in the composition due to precipitation, or other reasons. In each case, the SAM-e was mixed into a first material, denoted solvent A, in an attempt to at least partially solubilize the SAM-e in a first mixture, then the first mixture was attempted to be incorporated into a base that is typically in the form of an emulsion. In each case, SAM-e was first added to the solvent (A) then incorporated into the base (B), giving the result (C). The amount of SAM-e, solvent and base was selected to yield a final composition having the target minimal concentration of 35% wt/st SAM-e. In each of the following failed formulations, an attempt was made to form a stable composition by dissolving 40 g of SAM-e (free base) in 40 g of the "solvent" and then adding the specified "base" to bring the composition to 40% wt/wt SAM-e.

FORMULATIONS THAT FAIL

Batch 1.
A. Solvent: De-ionized water and filter purified water.
B. Base: Propylene glycol, polydiemthylsiloxane, SD alcohol, simethicone, phenoxyethanol, carbomer, vitamin E acetate, sodium hydroxide.
C. Result: Failed in approximately 12 hours due to separation and discoloration of ingredients within approximately 12 hours whether stored at room temperature or refrigerated at about 4° C.

Batch 2.
A. Solvent: De-ionized and purified water.
B. Base: Propylene glycol, ethoxydiglycol, vitamin E acetate, SD alcohol, aloe vera, caprylic triglyceride, sodium hydroxide.
C. Result: Failure in about 6 hours at room temperature and after refrigeration.

Batch 3.
A. Solvent: 70% isopropyl alcohol.
B. Base: Propylene glycol, polydiemthylsiloxane, SD alcohol, simethicone, phenoxyethanol, carbomer, vitamin E acetate, sodium hydroxide.
C. Result: Immediate batch failure within 5 minutes, no refrigeration attempted due to immediate failure.

Batch 4.
A. Solvent: Ethoxydiglycol.
B. Base: Propylene glycol, polydiemthylsiloxane, SD alcohol, simethicone, phenoxyethanol, carbomer, vitamin E acetate, sodium hydroxide.

C. Result: Failure at 12-15 hours at room temperature, failure upon refrigeration in 18 hours (note, once sample reached room temperature, separation occurred within 1 hour).

Batch 5.
A. Solvent: Ethoxydiglycol.
B. Base: Propylene glycol, ethoxydiglycol, vitamin E acetate, SD alcohol, aloe vera, caprylic triglyceride, sodium hydroxide.
C. Result: Failure at room temperature within 18 hours and failure upon refrigeration within 24 hours.

Batch 6.
A. Solvent: Glycerin (Synthetic).
B. Base: White petrolatum, cetyl alcohol, polysorbate 80, sodium lauryl sulfate, propylene glycol, urea, methylparaben, propylparaben.
C. Result: Failure due to uneven consistency and incomplete dissolution.

Batch 7.
A. Solvent: Glycerin (Synthetic).
B. Base: Propylene glycol, ethoxydiglycol, ethoxymethylcellulose, sodium hydroxide, methylparaben, propylparaben, imidazolidinyl urea, water.
C. Result: Failure within 24 hours upon refrigeration.

Batch 8.
A. Solvent: PLURONIC®F127 block copolymer surfactant.
B. Base: Purified water, imidazolidinyl urea, vitamin A palmitate, sodium hydroxide, aloe vera.
C. Result: Stable at 72 hours but had tacky consistency incompatible with patient acceptance; refrigeration caused preparation to be too viscous to apply (stability time unknown on refrigeration).

Batch 9.
A. Solvent: PLURONIC F127 block copolymer surfactant.
B. Base: Ethyl alcohol 190 proof, edetate disodium dehydrate, cetyl alcohol, stearyl alcohol, stearic acid, glyceryl monostearate, isopropyl myristate, simethicone, urea, polyoxyl 40 stearate, methylparaben, propylparaben, purified water. (PCCA VANPEN® base, PCCA, Houston Tex.).
C. Result: Stable for about 7 days but not pharmaceutically elegant. Increased humidity caused precipitation of SAM-e from preparation.

Batch 10.
A. Solvent: Lecithin soya granular.
B. Base: Isopropyl palmitate NF, sorbic acid NF.
C. Result: Failure within 60 minutes (no further variations attempted with base).

Batch 11.
A. Solvent: Almond oil NF.
B. Base: PCCA COSMETIC HRT® base.
C. Result: Failure within 2 hours and complete separation of ingredients.

Batch 12.
A. Solvent: Olive oil NF.
B. Base: PCCA COSMETIC HRT® base.
C. Result: Failure within 60 minutes and complete separation of ingredients.

Batch 13.
A. Solvent: De-ionized water.
B. Base: PCCA COSMETIC HRT® base.
C. Result: Stable for about 2-3 hours then complete dissolution in room temperature and refrigeration.

Batch 14.
A. Solvent: De-ionized water.
B. Base: PCCA LIPODERM™ lipophilic liposomic cream.
C. Result: Stable for 3 days then separation of ingredients occurred.

Batch 15
A. Solvent: De-ionized water.
B. Base: PCCA COSMETIC HRT® base adjusted to pH 7.0 with NaOH, KRISGEL™ 100 thickening agent.
C. Result: Separation of SAM-e from base in about 14 days.

Batch 16.
A. Solvent: De-ionized water.
B. Base: PCCA LIPODERM™ lipophilic liposomic cream base buffered to pH 7.0 with sodium hydroxide.
C. Result: Stability failure in 14 days at room temperature.

Batch 17.
A. Solvent: De-ionized water.
B. Base: PCCA LIPODERM™ lipophilic liposomic cream base buffered to pH 7.0 with Trolamine.
C. Result: Stable past 14 days at room temperature although not pharmaceutically elegant because it left residue left on the skin.

Analysis of the foregoing indicated that in contrast to cosmetic and other low dose compositions of SAM-e used in the prior art for other purposes, forming a suitable topical delivery composition with SAM-e present in amounts of at least 35% wt/wt for the purpose of treating depression cannot be readily accomplished using typical solvent systems without modification. To be commercially suitable, the compositions should be stable for at least 30 days when stored at room temperature or when stored in a refrigerator.

The following Examples illustrate suitable compositions for forming a stable SAM-e formulation for topical administration for treating depression: In each example, instead of dissolving the SAM-e in a solvent first, the SAM-e was milled into a base emulsion, then diluted with the "diluent" to a concentration of 40% wt/wt.

EXAMPLE 1

Batch 18.
A. Base: LIPODERM™ lipophilic liposomic cream base (SAM-e was incorporated into an equal weight of LIPODERM™ lipophilic liposomic cream to form a paste).
B. Diluent: LIPODERM™ lipophilic liposomic cream base (used to bring to final concentration of 40%).
C. Result: stable for 30 days. Elegant preparation with no visible residue left on skin. Tested for therapeutic efficacy which showed positive results.

EXAMPLE 2

Batch 19.
A. Base: PCCA LIPODERM™ lipophilic liposomic cream.
B. Diluent: PCCA LIPODERM™ lipophilic liposomic cream buffered to pH 6.8 with trolamine (triethanolamine) along with niacinamide for bacteriostatic effect and pyridoxine HCl for its vasodilatory properties. Final product was micronized using an ointment mill then put into air-tight oral syringes that are protective from light exposure then stored under refrigeration.
C. Result: Stable beyond 30 days.

EXAMPLE 3

Batch 20.
- A. Base: PCCA LIPODERM™ lipophilic liposomic cream buffered with trolamine, essential oil of cedar to mask the sulfur-like odor of SAM-e.
- B. Diluent: PCCA LIPODERM™ lipophilic liposomic cream buffered to pH 6.8 with Trolamine along with niacinamide for bacteriostatic effect and pyridoxine HCl for its vasodilatory properties. Final product was micronized using an ointment mill.
- C. Result: Stable, eloquent, therapeutically acceptable batch sorted under refrigeration beyond 30 days.

Subsequent batches The following examples each illustrate batches based on the composition of Example 3 but made with one or more additional ingredients to improve stability, penetration, fragrance, surface tension, antibacterial or antioxidant properties.

EXAMPLE 4

Batch 21
Same combination as in Example 3, but CoEnzyme Q10 was added
Result, functional but no additional benefit was noticeable, In addition batch left an orange-hue to skin.

EXAMPLE 5

Batch 22
Same combination as in Example 3 but 1, 3 glucan added for its antifungal and antioxidant properties
Result functionally stable but resulted in a gritty, pharmaceutically inelegant product.

EXAMPLE 6

The following Example is provided to show the ingredients and procedures for one specific embodiment of the delivery system provided herein.

| | |
|---|---|
| SAM-e powder | 40 g (free base) |
| Pyridoxyl-5-Phosphate | 1.0 g |
| Niacinamide | 2.0 g |
| KRISGEL ™ 100 thickening agent | 8.0 ml |
| Triethanolamine | 8.0 ml |
| Cinnamon leaf oil | 0.2 ml |
| Deoxy-d-glucose-(2) | 0.2 g |
| LIPODERM ™ lipophilic liposomic cream | 40 g (to start, and additional amounts to bring composition to 100 g total weight). |

The environmental conditions for formulating the composition was adjusted to a temperature of 65-75° F. and a relative humidity of less than 40%. Forty (40) g of SAM-e (free base) was ground into a fine powder and mixed with 40 g of LIPODERM™ lipophilic liposomic cream until all the SAM-e appeared to dissolve. The pyridoxal-5-phosphate and niacinamide were added and mixed until completely dissolved. The composition was then milled using an ointment mill to micronize undissolved SAM-e particles. This process decreases the particle size of SAM-e, thereby increasing the capacity for absorption through the skin. Trolamine, (triethanolamine) was added to adjust and buffer the pH to between 6.8 to 7.2, then deoxy-D-Glucose was added, followed by the cinnamon oil. KRISGEL™ 100 thickening agent was then added as a thickening agent to bring the composition to a desired viscosity. Finally, additional LIPODERM™ lipophilic liposomic cream was added to bring the concentration of the SAM-e to 40% wt/wt of the composition. The pyridoxyl-5-phosphate (vitamin B6) and niacinamide are used for vasodilation, which enhances the absorption of SAM-e. The cinnamon leaf oil is used to mask the odor of the SAM-e. Deoxy-d-glucose functions simultaneously as an anti-oxidant, anti-bacterial and anti-fungal preservative. The composition is stored in a refrigerator and is stable for at least 180 days.

From the foregoing it will be appreciated that, although specific embodiments of the invention have been described herein for purposes of illustration, various modifications may be made without deviating from the spirit and scope of the invention. Accordingly, the invention is not limited except as by the following claims.

What is claimed is:

1. A transdermal composition comprising
    an emulsion that includes a lipophilic component and an aqueous component;
    S-adenosyl methionine at least partially dissolved in the emulsion, wherein the amount of S-adenosyl methionine is at least 35% wt/wt of the composition;
    a pH adjusting component to bring the pH of the composition between 6.5 and 7.5;
    a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and
    the composition being formulated to be stable against separation of the emulsion for a period of at least 30 days when stored at room temperature.

2. The composition of claim 1, wherein the emulsion contains 55%-85% of the aqueous component and 45%-15% of the lipophilic component.

3. The composition of claim 1, wherein the emulsion contains 65%-75% of the aqueous component and 35%-25% of the lipophilic component.

4. The composition of claim 1, wherein the emulsion can be a lotion, a cream or a paste.

5. The composition of claim 1, wherein the amount of S-adenosyl methionine is at least 40% wt/wt of the composition.

6. The composition of claim 1, wherein the vasodilating agent is pyridoxal phosphate or niacinamide.

7. The composition of claim 1, further including an anti oxidizing agent.

8. The composition of claim 7, wherein the anti oxidizing agent is deoxy-D-glucose or vitamin E.

9. The composition of claim 1, further including a fragrant agent.

10. The composition of claim 9, wherein the fragrant agent comprises cinnamon oil.

11. The composition of claim 1, further including at least one of an antibacterial and an antifungal agent.

12. The composition of claim 11, wherein the antibacterial and antifungal agent is deoxy-D-glucose.

13. The composition of claim 1, formulated as a cream.

14. The composition of claim 1, formulated as a lotion.

15. The composition of claim 1, further including a gel thickening agent.

16. The composition of claim 1, wherein the lipophilic component includes at least 3 lipophilic substances which can be lecithin, C12-C15 alkyl benzoate, palmitate, isopropyl palmitate, vitamin A palmitate, vitamin C palmitate, butylated hydroxytoluene, cetyl alcohol, stearyl alcohol, stearic acid, glyceryl monostearate, isopropyl myristate, simethicone, polyoxyl stearate, glyceryl stearate, cetearyl alcohol, cetearyl glucoside, cetyl alcohol, bitter almond kernel oil, grape seed extract or wheat germ oil.

17. The composition of claim 15, wherein the emulsion includes ethylenediamine tetraacetic acid.

18. A transdermal composition comprising
an emulsion that includes a 15%-45% wt/wt of a lipophilic component and 55%-85% wt/wt of an aqueous component;
S-adenosyl methionine at least partially dissolved in the emulsion, wherein the amount of S-adenosyl methionine is at least 35% wt/wt of the composition;
a buffering agent;
a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and
the composition being formulated to be stable against separation of the emulsion for a period of at least 30 days when stored at room temperature.

19. A transdermal composition comprising an emulsion that includes a lipophilic component and an aqueous component;
S-adenosyl methionine, in an amount effective for treating depression, partially dissolved in a first portion of the lipophilic component, partly dissolved in a first portion of the aqueous component, partly encapsulated in micelles comprising a second portion of the lipid component surrounding a second portion of the aqueous component;
a pH adjusting component to bring the pH of the composition between 6.5 and 7.5;
a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and
the composition being formulated to be stable against separation of the emulsion for a period of at least 30 days when stored at room temperature.

20. A method for treating depression, comprising topically administering to a subject having depression, a composition according to claim 1.

21. A method of making a composition for treatment of depression by topical administration of S-adenosyl methionine comprising:
preparing the composition in a humidity controlled environment of about less than 40% humidity and at temperatures from between about 65° F. to about 75° F., in the following order:
mixing at least 35% wt/wt S-adenosyl methionine of the composition into an emulsion comprising 15%-45% wt/wt of a lipophilic component and 55%-85% wt/wt of an aqueous component, to form a paste comprising partially dissolved and partially suspended S-adenosyl methionine;
milling the paste until the partially suspended S-adenosyl methionine is not detectable in the paste by unaided visual inspection;
mixing into the paste a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and
diluting the milled paste with a diluent, wherein the paste and diluent are selected to provide an emulsion that is stable from separation when stored for at least 30 days at room temperature, such that the composition is suitable for transdermal delivery of S-adenosyl methionine into the subject's bloodstream for a systemic effect for the treatment of depression.

22. A transdermal composition comprising:
an emulsion comprising, a lipophilic component and an aqueous component;
S-adenosyl methionine at least partially dissolved in the emulsion, wherein the amount of S-adenosyl methionine is at least 35% wt/wt of the composition;
a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and
the composition being formulated to be stable against separation of the emulsion for a period of at least 30 days when stored at room temperature.

23. The composition of claim 22, wherein the emulsion comprises 55%-85% of the aqueous component and 15%-45% of the lipophilic component.

24. The composition of claim 22, wherein the emulsion comprises 65%-75% of the aqueous component and 25%-35% of the lipophilic component.

25. The composition of claim 22, further comprising a fragrant agent.

26. The composition of claim 25, wherein the fragrant agent comprises cinnamon oil.

27. The composition of claim 22, formulated as a cream.

28. A transdermal composition comprising:
an emulsion comprising 15%-45% wt/wt of a lipophilic component and 55%-85% wt/wt of an aqueous component;
S-adenosyl methionine, in an amount effective for treating depression;
a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and
the composition being formulated to be stable against separation of the emulsion for a period of at least 30 days when stored at room temperature.

29. The composition of claim 28, wherein the S-adenosyl methionine is present in an amount of at least 35% wt/wt of the composition.

30. The composition of claim 28, wherein the emulsion comprises 65%-75% wt/wt of the aqueous component and 25%-35% wt/wt of the lipophilic component.

31. The composition of claim 28, further comprising a fragrant agent.

32. The composition of claim 31, wherein the fragrant agent comprises cinnamon oil.

33. The composition of claim 28, formulated as a cream.

34. A transdermal composition comprising:
an emulsion comprising a lipophilic component and an aqueous component;
S-adenosyl methionine, in an amount effective for treating depression, partially dissolved in a first portion of the lipophilic component, partly dissolved in a first portion of the aqueous component, partly encapsulated in micelles comprising a second portion of the lipid component surrounding a second portion of the aqueous component;
a vasodilating agent which can be pyridoxal-5-phosphate, niacinamide, dimethyl sulfoxide, pentoxifylline, ibuprofen, horse chestnut extract (*Aesculus hippocastanum*) or pyridoxine; and the composition being formulated to be stable against separation of the emulsion for a period of at least 30 days when stored at room temperature.

35. The composition of claim 34, wherein the S-adenosyl methionine is present in an amount of at least 35% wt/wt of the composition.

36. A method for treating depression, comprising topically administering to a subject having depression, a composition according to claim 22.

37. A method of making a composition for topical administration of S-adenosyl methionine comprising:
preparing the composition in a humidity controlled environment of about less than 40% humidity and at temperatures from between about 65° F. to about 75° F., in the following order:
mixing a weight of S-adenosyl methionine in an amount effective for treating depression into an emulsion comprising 15%-45% wt/wt of a lipophilic component and 55%-85% wt/wt of an aqueous component, to form a paste comprising partially dissolved and partially suspended S-adenosyl methionine;
milling the paste until the partially suspended S-adenosyl methionine is not detectable in the paste by unaided visual inspection;
mixing into the paste a vasodilating agent which can be pyridoxal-5-phosphate, niacinamide, dimethyl sulfoxide, pentoxifylline, ibuprofen, horse chestnut extract (*Aesculus hippocastanum*) or pyridoxine;
diluting the milled paste with a diluent; and
adding a buffering agent to the composition, wherein the emulsion and diluent are selected to provide the composition that is stable from separation when stored for at least 30 days at room temperature, such that the composition is suitable for transdermal delivery of S-adenosyl methionine into the subject's bloodstream for a systemic effect for the treatment of depression.

38. The composition of claim 18, wherein the vasodilating agent is pyridoxal phosphate or niacinamide.

39. The composition of claim 19, wherein the vasodilating agent is pyridoxal phosphate or niacinamide.

40. The method of claim 21, wherein the vasodilating agent is pyridoxal phosphate or niacinamide.

41. The composition of claim 22, wherein the vasodilating agent is pyridoxal phosphate or niacinamide.

42. The composition of claim 28, wherein the vasodilating agent is pyridoxal phosphate or niacinamide.

43. The composition of claim 34, wherein the vasodilating agent is pyridoxal phosphate or niacinamide.

44. The method of claim 37, wherein the vasodilating agent is pyridoxal phosphate or niacinamide.

45. A transdermal composition comprising:
an emulsion comprising a lipophilic component and an aqueous component;
S-adenosyl methionine partially dissolved in a first portion of the lipophilic component, partly dissolved in a first portion of the aqueous component, partly encapsulated in micelles comprising a second portion of the lipid component surrounding a second portion of the aqueous component, wherein the amount of S-adenosyl methionine is at least 35% wt/wt of the composition;
a buffering agent; and
the composition being formulated to be stable against separation of the emulsion for a period of at least 30 days when stored at room temperature.

46. The composition of claim 45, wherein the buffering agent is triethanolamine.

47. The composition of claim 45, wherein the buffering agent maintains the pH of the composition between about 6.5 and about 7.5.

48. A transdermal composition comprising:
an emulsion comprising a lipophilic component and an aqueous component;
S-adenosyl methionine, wherein the amount of S-adenosyl methionine is at least 35% wt/wt of the composition;
a buffering agent; and
the composition being formulated to be stable against separation of the emulsion for a period of at least 30 days when stored at room temperature.

49. A method for treating depression in a subject, comprising:
administering to a subject having depression, an effective amount of a transdermal composition to deliver S-adenosyl methionine directly into the subject's bloodstream for a systemic effect, the composition comprising:
an emulsion comprising, a lipophilic component and an aqueous component; and
S-adenosyl methionine at least partially dissolved in the emulsion, wherein the amount of S-adenosyl methionine is at least 35% wt/wt of the composition; and
the composition being formulated to be stable against separation of the emulsion for a period of at least 30 days when stored at room temperature, thereby treating depression in the subject.

50. The method of claim 49, wherein the composition further comprises a vasodilating agent which can be pyridoxal-5-phosphate, niacinamide, dimethyl sulfoxide, pentoxifylline, ibuprofen, horse chestnut extract (*Aesculus hippocastanum*) or pyridoxine.

\* \* \* \* \*